(12) United States Patent
Gustavsson (10) Patent No.: US 9,849,304 B2
(45) Date of Patent: Dec. 26, 2017

(54) DEVICE AND METHOD FOR TREATMENT OF ORGANIC TISSUE

(75) Inventor: Morgan Lars Ake Gustavsson, Newton, MA (US)

(73) Assignee: Gustavsson Nevada Holding LLC, Las Vegas, NV (US)

( * ) Notice: Subject to any disclaimer, the term of this patent is extended or adjusted under 35 U.S.C. 154(b) by 2794 days.

(21) Appl. No.: 12/184,821

(22) Filed: Aug. 1, 2008

(65) Prior Publication Data

US 2009/0036953 A1 Feb. 5, 2009

Related U.S. Application Data

(60) Provisional application No. 60/953,611, filed on Aug. 2, 2007.

(51) Int. Cl.
| | | |
|---|---|---|
| *A61N 5/06* | (2006.01) | |
| *A61B 18/20* | (2006.01) | |
| *A61B 18/00* | (2006.01) | |
| *A61N 5/067* | (2006.01) | |

(52) U.S. Cl.
CPC .......... *A61N 5/0616* (2013.01); *A61B 18/203* (2013.01); *A61B 2018/00005* (2013.01); *A61B 2018/00452* (2013.01); *A61N 2005/067* (2013.01)

(58) Field of Classification Search
CPC ............ A61N 5/0616; A61N 2005/067; A61B 18/203; A61B 2018/00005; A61B 2018/00452
USPC ...................................... 607/88–93
See application file for complete search history.

(56) References Cited

U.S. PATENT DOCUMENTS

| | | | |
|---|---|---|---|
| 4,499,403 A | 2/1985 | Leppelmeier et al. | |
| 5,026,366 A | 6/1991 | Leckrone | |
| 5,320,618 A | 6/1994 | Gustafsson | |
| 5,620,478 A | 4/1997 | Eckhouse | |
| 5,626,631 A | 5/1997 | Eckhouse | |
| 5,720,772 A | 2/1998 | Eckhouse | |
| 5,755,751 A | 5/1998 | Eckhouse | |
| 6,413,268 B1 | 7/2002 | Hartman | |
| 6,443,946 B2 | 9/2002 | Clement et al. | |
| 6,514,243 B1 | 2/2003 | Eckhouse et al. | |
| 6,981,970 B2 | 1/2006 | Karni | |
| 7,083,610 B1 * | 8/2006 | Murray et al. ................... 606/9 |
| 2002/0067121 A1 * | 6/2002 | Jean et al. ................... 313/485 |

(Continued)

FOREIGN PATENT DOCUMENTS

| | | |
|---|---|---|
| DE | 103 35 303 | 2/2004 |
| EP | 0 586 353 | 3/1994 |

OTHER PUBLICATIONS

International Search Report for International Application No. PCT/US2008/071963, dated Dec. 5, 2008 (5 pages).

*Primary Examiner* — Heidi M Eide
(74) *Attorney, Agent, or Firm* — Knobbe, Martens, Olson & Bear, LLP.

(57) ABSTRACT

An optic includes a first end, a fluorescent material, and a second end. The first end is adapted to transmit a first band of electromagnetic radiation to the fluorescent material. The fluorescent material is adapted to absorb the first band of electromagnetic radiation and emit a second band of electromagnetic radiation. The second end is adapted to contact the biological tissue and deliver the second band of electromagnetic radiation to treat the biological tissue.

15 Claims, 3 Drawing Sheets

(56) References Cited

U.S. PATENT DOCUMENTS

2003/0044114 A1 3/2003 Pelka
2006/0020309 A1 1/2006 Altshuler et al.

\* cited by examiner

DEVICE AND METHOD FOR TREATMENT OF ORGANIC TISSUE

CROSS-REFERENCE TO RELATED APPLICATIONS

This application claims benefit of priority to Application No. 60/953,611, filed Aug. 2, 2007 and entitled "Device and method for treatment of organic tissue" by Gustavsson, the disclosure of which is incorporated herein by reference in its entirety.

FIELD OF THE INVENTION

In general, the invention relates to methods and apparatuses for treating biological tissue with electromagnetic radiation. In particular, the invention relates to methods and apparatuses including an optic that absorbs a first band of electromagnetic radiation and emits a second band of electromagnetic radiation for treating biological tissue.

BACKGROUND OF THE INVENTION

Numerous methods and apparatus exist for treating biological tissue with electromagnetic radiation that is derived from a fluorescent light source. For example:

U.S. Pat. No. 6,981,970 discloses an epilation method using light produced by a fluorescent material pumped with ultraviolet light from an ultraviolet light source. In one embodiment, light passes along a path through a fluorescent block, and then though a filter to prevent unwanted wavelengths of light from reaching the skin. In other embodiments light passes along a first path to a fluorescent block, and then in a second perpendicular path to the skin.

U.S. Pat. No. 6,902,563 discloses an irradiation device for therapeutic treatment of skin. The device transforms the UV parts of the spectrum emitted by a light source using various kinds of foil (e.g., silicone elastomers or fluorpolymers, particularly PTFE (e.g., TEFLON®), doped with anorganic phosphors). Undesired portions of the emission spectrum can be removed using a filter.

U.S. Pat. No. 7,208,007 discloses a fluorescence concentrator system that provides for a high brightness light source. The system can include a host doped with fluorescent material, which is optically pumped by an adjacent illumination source. The fluorescence concentrator captures a portion of the isotropically emitted fluorescent light and guides it to an output surface. Light from the lamp that does not interact with the fluorescence concentrator passes through the concentrator and is not directed to the skin. Filters can be used to eliminate undesired wavelengths.

U.S. Pat. No. 5,320,618 discloses a device for the treatment of undesired superficial skin afflictions. The device includes a light source for producing light including a first predetermined wavelength, a light transforming means (e.g., fluorescent dye) for transforming the first predetermined wavelength to a second predetermined wavelength, and a guide means for directing the second predetermined wavelength to a predetermined location (e.g., tissue).

U.S. Pat. No. 7,252,628 discloses a device for treating human skin with radiation. A radiation filter is provided in the radiation path. The radiation filter includes water which is in solid state at least during an initial phase of operation of the device. The radiation filter can contact the skin and can include a fluorescent dye.

U.S. Pat. No. 7,083,610 discloses a device for irradiating tissue including a fluorescent element positioned to receive pump radiation having a narrow spectral band and responsively generate radiation by spontaneous emission, the fluorescent element delivering at least a portion of the diffuse emitted radiation toward a tissue target. The device also includes a substantially transparent window having a proximal face positioned adjacent to the fluorescent element and a distal face for contacting the target.

However, these methods and apparatuses produce wavelengths of light (e.g., from the light source, which travel unaltered to the biological tissue) that are harmful, non-therapeutic, or otherwise undesirable for treating biological tissue. Therefore, these methods and apparatuses are complicated and hindered by means for preventing these undesirable wavelengths from reaching the biological tissue. For example, these methods and apparatuses can require a filter between the fluorescent material and the biological tissue to prevent undesirable wavelengths from reaching the biological tissue. Further, these methods and apparatus can require an arrangement where light travels substantially along two perpendicular axes, one from the light source to the fluorescent body and another from the fluorescent body to the biological tissue.

BRIEF SUMMARY OF THE INVENTION

The invention, in various aspects and embodiments, includes apparatuses, methods, and kits that can be used for therapeutic treatments of biological tissue. Apparatuses include an optic having a first end, a fluorescent material, and a second end. The first end is adapted to transmit a first band of electromagnetic radiation to the fluorescent material. The fluorescent material is adapted to absorb the first band of electromagnetic radiation and emit a second band of electromagnetic radiation. The second end is adapted to contact the biological tissue and deliver the second band of electromagnetic radiation to treat the biological tissue. Methods include techniques for using the apparatuses for therapeutic treatments of biological tissue, techniques for physio-chemically modifying an object with electromagnetic radiation, and techniques for using the apparatuses for providing electromagnetic radiation capable of treating biological tissue. Kits include apparatuses, together with additional items such as instruction, for facilitating therapeutic treatments.

In some aspects and embodiments, the invention includes an optic that directly contacts the biological tissue (e.g., without the use of a filter or a light guiding means disposed between the optic and the biological tissue). Furthermore, in certain aspects and embodiments, electromagnetic radiation (e.g., light) travels substantially along a single axis from the light source to the fluorescent body, and further to the tissue. In each case, such an arrangement can be possible because wavelengths of electromagnetic radiation that are harmful, non-therapeutic, or otherwise undesirable do not reach and/or do not pass through the optic to the biological tissue. Accordingly, the invention provides apparatuses, methods, and kits that can be more effective, safer, easier to maintain, easier to operate, and more cost effective than conventional technologies, and that can provide therapeutic treatments of biological tissue that are not otherwise possible or practicable using conventional technologies.

Therapeutic treatments include treatments for disease (e.g., any medical condition caused by a pathogen, genetics, injury, and the like) and cosmetic treatments (e.g., any condition desired by a patient for cosmetic reasons, even where not medically necessary). In various embodiments, the biological tissue is skin or structures or conditions therein. Biological tissue can also include any one or more of hair follicles, fatty tissue, vasculature, glands, ducts, and vessels. Conditions and treatments can include hair removal, reduction, or regrowth (each either temporary or permanent), vascular lesions, pigmented lesions, bruising, unwanted fat, water retention, tattoo removal, pores, wrinkles and fine lines, dyschromia (e.g., skin discoloration), infection (e.g., bacterial, viral, eukaryotic, or fungal), inflammation, infestation, pain, acne, cellulite, psoriasis, and vitiligo.

In one aspect, the invention features an optic having a first end, a fluorescent material, and a second end. The first end is adapted to transmit a first band of electromagnetic radiation to the fluorescent material. The fluorescent material is adapted to absorb the first band of electromagnetic radiation and emit a second band of electromagnetic radiation. The second end is adapted to contact the biological tissue and deliver the second band of electromagnetic radiation to treat the biological tissue.

In another aspect, the invention features an apparatus for treating biological tissue. The apparatus includes an optic having a first end, a second end, and a fluorescent material. The fluorescent material is adapted to substantially absorb a first band of electromagnetic radiation and emit a second band of electromagnetic radiation. The apparatus also includes a filter disposed relative to the first end of the optic and adapted to substantially transmit the first band of electromagnetic radiation to the fluorescent material and to block other electromagnetic radiation. The second end of the optic is for contacting the biological tissue and delivering the second band of electromagnetic radiation to treat the biological tissue.

In still another aspect, the invention features a method for treating biological tissue. The method includes contacting the biological tissue with an optic having a fluorescent material adapted to substantially absorb a first band of electromagnetic radiation and to emit a second band of electromagnetic radiation. The method also includes delivering the first band of electromagnetic radiation to the optic, to cause the optic to emit the second band of electromagnetic radiation. Furthermore, the method includes delivering the second band of electromagnetic radiation to treat the biological tissue.

In yet another aspect, the invention features a method for physio-chemically modifying an object with electromagnetic radiation. The method includes contacting the object with an optic having a fluorescent material adapted to substantially absorb a first band of electromagnetic radiation and to emit a second band of electromagnetic radiation. The method also includes delivering the first band of electromagnetic radiation to the optic, to cause the optic to emit the second band of electromagnetic radiation. Furthermore, the method includes delivering a predetermined amount of the second band of electromagnetic radiation to the object.

In still yet another aspect, the invention features a method for providing electromagnetic radiation capable of treating biological tissue. The method includes contacting the biological tissue with a device including an optic, the optic having a fluorescent material adapted to substantially absorb a first band of electromagnetic radiation and to emit a second band of electromagnetic radiation. The method also includes delivering the first band of electromagnetic radiation to the optic, to cause the optic to emit the second band of electromagnetic radiation.

In still yet another aspect, the invention features a kit for treating biological tissue. The kit includes an apparatus including (i) an optic having a first end, a second end, and a fluorescent material, the fluorescent material adapted to substantially absorb a first band of electromagnetic radiation and emit a second band of electromagnetic radiation and (ii) a filter disposed relative to the first end of the optic and adapted to substantially transmit the first band of electromagnetic radiation to the fluorescent material and to block other of electromagnetic radiation. The kit also includes instruction means for contacting the biological tissue with a second end of the optic and delivering the second band of electromagnetic radiation to treat the biological tissue.

In other embodiments, any of the aspects above, or any apparatus, method, or kit described herein, can include one or more of the following features.

In one embodiment, the optic includes a second band reflector disposed relative to at least one surface of the optic. The second band reflector can reflect at least a portion of the second band of radiation, to direct the portion towards the biological tissue.

In various embodiments, the filter is a coating on a surface of the first end. The filter can be a dichroic element. In one embodiment, the filter can block a portion of the second band of electromagnetic radiation, to direct the portion towards the biological tissue.

In some embodiments, the apparatus includes a reflector disposed relative to a surface of the optic between the first end and the second end, the reflector adapted to reflect the second band of electromagnetic radiation.

In certain embodiments, the apparatus includes a light source disposed relative to the filter, the light source adapted to provide the first band of electromagnetic radiation. The apparatus can include a second reflector disposed relative to the light source, to direct a portion of the first band of electromagnetic radiation to the fluorescent material.

In various embodiments, a cooling element can be adapted to cool one or more of the biological tissue, the optic, the filter or any combination of the aforementioned. Further, separate cooling elements can be used to cool one or more of the biological tissue, the optic, the filter or any combination of the aforementioned.

In some embodiments, the apparatus includes an index matching element disposed relative to the second end, the index matching element adapted to facilitate delivering the second band of electromagnetic radiation to the biological tissue. Methods can include applying an index matching element between the optic and the biological tissue, to facilitate delivering the second band of electromagnetic radiation to the biological tissue.

In certain embodiments, the apparatus includes a second fluorescent material disposed relative to the filter.

In various embodiments, the second band of radiation is characterized by a fluence from about 1 $J/cm^2$ to about 100 $J/cm^2$. In some embodiments, the second band of radiation is characterized by a fluence from about 10 $J/cm^2$ to about 100 $J/cm^2$. The second band of electromagnetic radiation can be characterized by a pulse greater than about 1 ms. The second band of electromagnetic radiation can be characterized by a pulse width between about 1 ms and about 120 ms.

In some embodiments, the method includes applying pressure to substantially remove air intervening the biological tissue and the optic.

In certain embodiments, the fluorescent body is selected to emit the second band of electromagnetic radiation matched to a chromophore within the biological tissue.

In various embodiments, the method includes (i) delivering the first band of electromagnetic radiation through a filter disposed relative to a first end of the optic, the filter adapted to substantially transmit the first band of electromagnetic radiation to the fluorescent material and to block other electromagnetic radiation and (ii) delivering the second band of electromagnetic radiation to the biological tissue through a second end of the optic, the second end contacting the biological tissue. In one embodiment, the filter blocks a portion of the second band of electromagnetic radiation, to direct the portion towards the biological tissue.

In some embodiments, the method includes delivering a therapeutically effective amount of the second band of electromagnetic radiation to treat the biological tissue.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

The invention includes apparatuses, methods, and kits that can be used for therapeutic treatments of biological tissue. Apparatuses include an optic having a first end, a fluorescent material, and a second end. The first end is adapted to transmit a first band of electromagnetic radiation to the fluorescent material. The fluorescent material is adapted to absorb (e.g., absorb at least a portion of) the first band of electromagnetic radiation and emit a second band of electromagnetic radiation. The second end is adapted to contact the biological tissue and deliver the second band of electromagnetic radiation to treat the biological tissue. In various embodiments, the optic directly contacts the biological tissue without an intervening waveguide or filter.

Methods include techniques for using the apparatuses for therapeutic treatments of biological tissue, techniques for physio-chemically modifying an object with electromagnetic radiation, and techniques for using the apparatuses for providing electromagnetic radiation capable of treating biological tissue. Kits include apparatuses, together with additional items such as instruction, for facilitating therapeutic treatments.

Therapeutic treatments include treatments for disease (e.g., any medical condition caused by a pathogen, genetics, injury, inflammation, and the like) and cosmetic treatments (e.g., any condition desired by a patient for cosmetic reasons, even where not medically indicated). In various embodiments, the biological tissue is skin or structures or conditions therein. Biological tissue can also include any one or more of hair follicles, fatty tissue, vasculature, glands, ducts, and vessels. Conditions and treatments can include hair removal, reduction, or regrowth (each either temporary or permanent), vascular lesions, pigmented lesions, bruising, unwanted fat, water retention, tattoo removal, pores, wrinkles and fine lines, dyschromia (e.g., skin discoloration), infection (e.g., bacterial, viral, eukaryotic, or fungal), inflammation, infestation, pain, acne, cellulite, psoriasis, and vitiligo.

Figure 1:
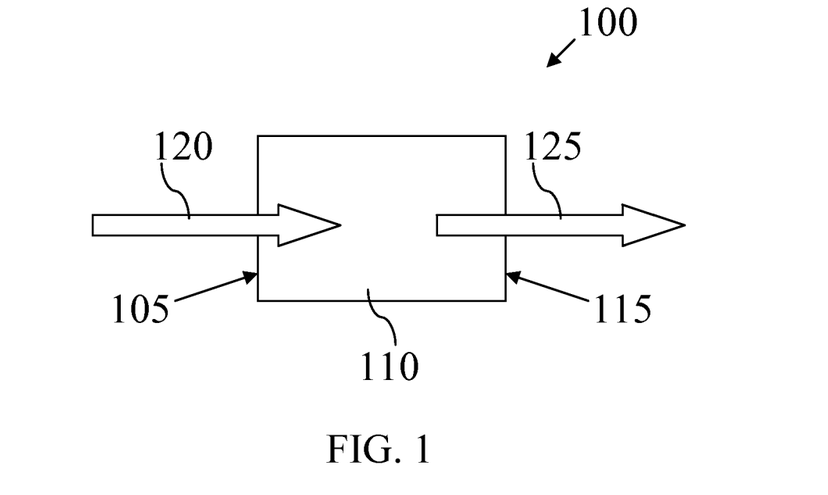
FIG. 1 shows an exemplary optic having a first end, a fluorescent material, and a second end.

FIG. 1 shows an exemplary optic 100 having a first end 105, a fluorescent material 110, and a second end 115. The first end 105 is adapted to transmit a first band 120 of electromagnetic radiation to the fluorescent material 110. The fluorescent material 110 is adapted to absorb (e.g., absorb at least a portion of) the first band 120 of electromagnetic radiation and emit a second band 125 of electromagnetic radiation. In various embodiments, the fluorescent material 110 substantially absorbs (e.g., greater than about 80%, greater than about 90%, or about 100% of) the first band 120 of electromagnetic radiation. The second end 115 is adapted to be positioned relative to the biological tissue and deliver the second band 125 of electromagnetic radiation to treat the biological tissue. For example, the second end 115 can be positioned adjacent to, contacting, or touching the biological tissue either directly or though an index matching element (e.g., a non-light guide, non-filtering liquid or gel). However, a light guide is not necessary to couple the second band 125 into the biological tissue. In this, and other exemplary embodiments, band can refer to a single wavelength (e.g., when used in conjunction with a coherent light source) or multiple wavelengths within a range (e.g., when used in conjunction with an incoherent light source). In one embodiment, the optic 100 also includes a second band reflector (not shown) disposed relative to at least one surface of the optic. The second band reflector can reflect at least a portion of the second band of radiation, to direct the portion towards the biological tissue.

In various embodiments, the fluorescent material 110 includes a fluorescent crystal, glass, polymer, liquid, or dye. In general, the fluorescent substance is capable of modulating (e.g., transforming, converting, or varying) at least one property of the electromagnetic radiation. For example, the fluorescent substance can be a fluorescent crystal, glass, polymer, liquid, or dye selected to convert the electromagnetic radiation from at least one first wavelength to at least one second wavelength. In some embodiment, more than one fluorescent material 110 can be employed. Accordingly, at least one fluorescent material 110 can be selected depending upon the desired treatment and/or desired emission wavelength. Because the emission wavelength can be controlled by selecting one or more appropriate fluorescent material 110, the optic 100 does not require a filter to obtain a desired emission wavelength. The absorbing and emitting wavelengths of the fluorescent material 110 can be selected by the user or a technician. Since the optic 100 is in contact with or adjacent to the biologic tissue, no light guiding means between the body and the tissue need be used.

In various embodiments, the fluorescent material 110 is a fluorescent crystal, glass, or polymer. For example the fluorescent material 110 can include at least one of a Ti-sapphire, ruby, and alexandrite. The fluorescent material 110 can include a fluorescent glass such as LUMILASS-R7/G9/B manufactured by Sumita Optical Glass, Inc. The fluorescent material 110 can include a fluorescent polymer such as poly(methyl methacrylate) (PMMA) or polyurethane, which can include a fluorescent dye. The fluorescent material 110 can include a laser crystal such as a Nd:YAG crystal, or an erbium glass or crystal, or a uranium glass or crystal.

In various embodiments, the fluorescent material 110 can change blue-green light to yellow and/or red light. For example, the fluorescent material 110 can be a liquid dye such as pyrromethene, preferably pyrromethene 580, for changing light emitted from a source to a desired wavelength. A suitable concentration can be a concentration sufficient to achieve greater than about 80%, greater than about 90%, or about 100% absorption of electromagnetic radiation. The liquid base can be, for example, an alcohol or a mixture of alcohols, preferably methanol and/or ethanol. In various embodiments, the fluorescent substance can include 4-dicyanomethylene-2-methyl-6-(p(dimethylamino)styryl)-4H-pyran (DCM), pyrromethene, fluorescein, coumarin, stilbene, umbelliferone, tetracene, malachite green, rhodamin, or rhodamin 6G. In various embodiments, adamantane can be added to a fluorescent substance to prolong its life. In some embodiments, cycloheptatriene and cyclooctatetraene can be added to a fluorescent substance as triplet quencher, to increase output power. In certain embodiments, a fluorescent substance can include one or more pyrromethanes.

In various embodiments, harmful, non-therapeutic, or otherwise undesirable wavelength(s) of electromagnetic radiation do not pass through (e.g., no substantial or meaningful amount passes through) the optic and reach the biological tissue. The optic can be at least partially non-transparent to certain electromagnetic radiation emitted from a source of electromagnetic radiation (not shown), to prevent that certain wavelength(s) from reaching the biological tissue. Non-transparency (e.g., prevention of transmission by reflection or absorption) can be partial or complete, and can pertain to non-transparency to electromagnetic radiation having a particular spectrum, intensity, or both. The optic and source of electromagnetic radiation can be selected such that the fluorescent material 110 substantially absorb the electromagnetic radiation emitted from the source (e.g., the first band 120) and substantially converts that electromagnetic radiation into the second band 125 of electromagnetic radiation. For example, a Ti-sapphire (i.e., a fluorescent material) will substantially absorb the electromagnetic radiation emitted from a Nd:YAG laser operating at 532 nm (i.e., a first band of electromagnetic radiation, the absorption range is about 400 to about 600 nm) and substantially emit electromagnetic radiation at about 795 nm (i.e., the second band of electromagnetic radiation, the emission range is about 660 to about 1050 nm) for treating biological tissue.

The second end 115 is generally a smooth surface. However, other surfaces are possible. For example, the second end 115 can have a rough surface for diffusing the second band 125 of electromagnetic radiation (e.g., to alter the propagation of the electromagnetic radiation and/or to increase surface area for cooling).

Therefore, in this and other embodiments, the second end 115 can contact the biological tissue and deliver the second band 125 of electromagnetic radiation to treat the biological tissue because harmful, non-therapeutic, or otherwise undesirable wavelength(s) of electromagnetic radiation do not pass through the optic and reach the biological tissue. Furthermore, because of the contact between the second end and the biological tissue, as light guide is not necessary to couple the second band into the biological tissue. A filter disposed between the optic and the biological tissue is not necessary to remove the undesirable wavelength(s). Furthermore, in this and other embodiments, an apparatus can have an arrangement whereby light travels substantially a single axis, from the source of electromagnetic radiation, to the optic, and further to the biological tissue.

In various embodiments, a second band of electromagnetic radiation includes at least one wavelength between about 400 nm and about 2000 nm. The second band of electromagnetic radiation can be selected to be absorbed preferentially by a chromophore in the biological tissue (e.g., skin). The chromophore can include at least one of hemoglobin, melanin (e.g., any one or more of eumelanin, pheomelanin, and neuromelanin), porphyrin, collagen, exogenous pigment (e.g., tattoo ink), and water in the skin. The chromophore can absorb the electromagnetic radiation preferentially over adjacent skin tissue. The spectrum characterizing the electromagnetic radiation delivered to the biological tissue can be matched to an absorption spectrum of at least one of melanin, water, a porphyryn, whole blood, hemoglobin, reduced hemoglobin, and oxidized hemoglobin. Either the first band or second band of electromagnetic radiation can include a single wavelength or multiple wavelengths of radiation.

In various embodiments, the second band of electromagnetic radiation is characterized by an energy density between about 0.1 J/cm$^2$ and about 500 J/cm$^2$. In various embodiments, the electromagnetic radiation delivered to the biological tissue can be characterized by an energy density between about 1 J/cm and about 100 J/cm, about 1 J/cm and about 10 J/cm, about 2.5 J/cm$^2$ and about 60 J/cm$^2$, or about 2.5 J/cm$^2$ and about 12 J/cm$^2$. In certain embodiments, the energy density can be about 0.1, 0.51, 5, 10, 50, 100, 150, 200, 250, 300, 350, 400, or 450 J/cm$^2$, or any value therebetween.

In various embodiments, the second band of electromagnetic radiation can be characterized by a pulse width between about 10 µs and about 2 s. In one embodiment, the electromagnetic radiation is characterized by a pulse width between about 1 ms and about 120 ms. A pulse width can be about 10, 20, 30, 40, or 50 ms. In some embodiments, the second band of electromagnetic radiation is continuous (e.g., a pulse width of greater than about 2 s). A pulse width can be selected based upon the type of treatment and/or the type of skin being treated. Pulses can be single or repetitive, and can have a frequency between about 0.1 Hz and about 1000 Hz or between about 0.1 Hz and about 100 Hz. A second band of electromagnetic radiation can be characterized by a spot size between about 1 mm and about 20 mm. A spot size can be up to about 1, 2, 3, 4, or 5 mm in diameter. In various embodiments, the optic can produce a spot size of about 2 mm or greater in diameter. In general, the optical diameter of the optic and the second end are proportional to the diameter of the spot size when the second end is in contact with the skin.

In various embodiments, the optic 100, and other optics described and claimed herein, can have a length (e.g., generally linear although other geometries are possible) and a cross section (e.g., generally rectilinear or ellipsoid although other geometries are possible). For example, the length of an optic can be selected to substantially absorb (e.g., greater than about 80%, greater than about 90%, or about 100%) a first band of radiation. Accordingly, the length of an optic can vary (e.g., with absorption per unit length). However, a length of about 15 mm to about 20 mm is generally functional. The cross section of an optic is generally selected to produce a spot size and a shape desirable for treatment. In one example, a cross section can be a square or a circle with a diameter of about 20 mm. In another example, the cross section is four sided and each side has a length between about 20 mm and about 10 cm.

The optic 100 can have a cylindrical shape or can taper from one end to the second end. For example, the optic 100 can taper from the first end to the second end to facilitate delivery of the electromagnetic radiation to the skin.

Figure 2:
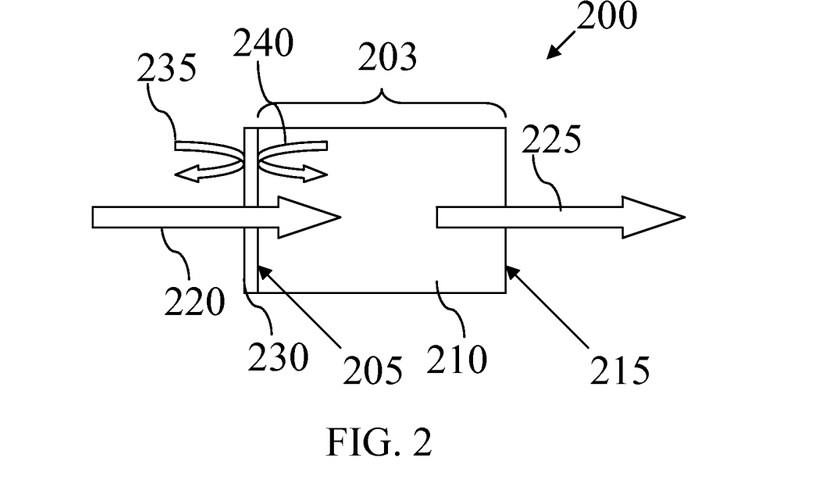
FIG. 2 shows an exemplary apparatus for treating biological tissue including an optic and a filter.

FIG. 2 shows an exemplary apparatus 200 for treating biological tissue including an optic 203 and a filter 230. The optic 203 has a first end 205, a second end 215, and a fluorescent material 210. The fluorescent material 210 is adapted to substantially absorb a first band 220 of electromagnetic radiation and emit a second band 225 of electromagnetic radiation. The second end of the optic 215 is for contacting biological tissue (not shown) and delivering the second band 225 of electromagnetic radiation to treat the biological tissue. The optic 203, first end 205, fluorescent material 210, second end 215, first band 220 of electromagnetic radiation, and second band 225 of electromagnetic radiation can include any one or more of the features of respective elements optic 100, first end 105, fluorescent material 110, second end 115, first band 120 of electromagnetic radiation, and second band 125 of electromagnetic radiation discussed in connection with FIG. 1.

The filter 230 is disposed relative to the first end 205 of the optic and is adapted to substantially transmit the first band 220 of electromagnetic radiation to the fluorescent material 210 and to block (e.g., reflect, absorb, or both) other electromagnetic radiation 235. Although the filter 230 is illustrated in contact with the first end 205, the filter can be positioned anywhere between the source of electromagnetic radiation and the first end 205. In various embodiments, the filter 230 can block a portion 240 of the second band 225 of electromagnetic radiation, to direct the portion 240 towards the biological tissue. In some embodiments, the filter 230 is embodied by an element functioning as a mirror (e.g., reflecting an undesired wavelength) or partial mirror. In certain embodiments, the filter 230 is embodied by an element functioning as an absorbing filter (e.g., absorbing an undesired wavelength). The filter 230 can also function as both a mirror and an absorbing filter. Blocking other electromagnetic radiation 235 and blocking a portion 240 of the second band 225 are separable functions (e.g., a filter 230 can have any one or both functions).

In various embodiments, a filter 230 can be a dichroic element, for example, a dichroic filter, thin-film filter, dichroic mirror, or dichroic reflector. A filter 230 can include one or more metal oxide layers. Examples of a filter 230 include the model number FF01-6804/SP filter available from SEMROCK®, Inc., as well as the BRIGHTLINE® filters also available from SEMROCK®, Inc. In one embodiment, the filter 230 reflects wavelengths greater than about 600 nm and less than about 440 nm.

The filter can be a coating on a surface of the first end of the optic. In some embodiments, the filter can be a coating on all surfaces of the optic except the second end of the optic.

Figure 3:
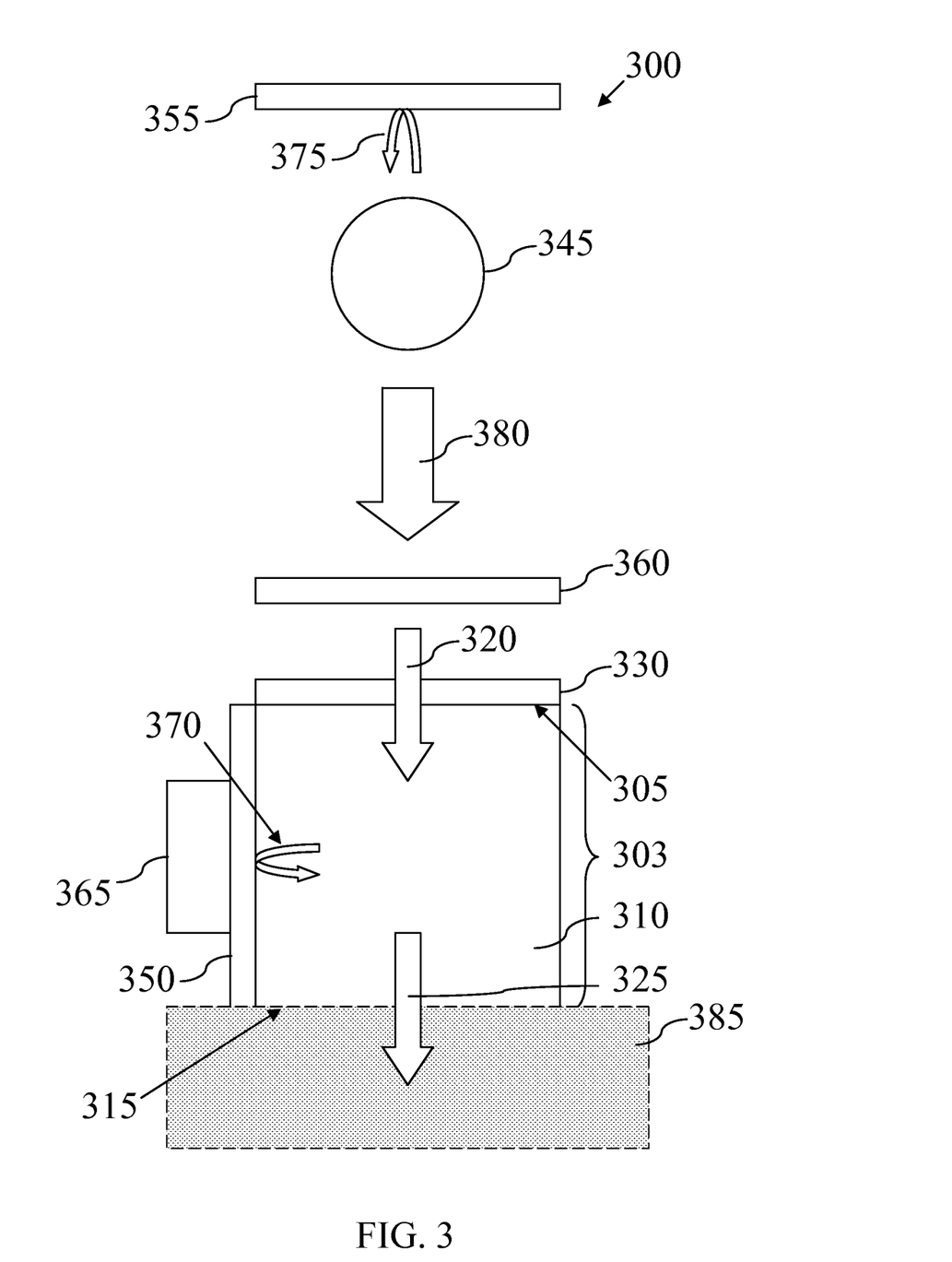
FIG. 3 shows an exemplary apparatus for treating biological tissue including elements from various different embodiments.

FIG. 3 shows various elements from various different embodiments in the context of an exemplary apparatus 300. The optic 303 has a first end 305, a second end 315, a fluorescent material 310, and a filter 330. The fluorescent material 310 is adapted to substantially absorb a first band 320 of electromagnetic radiation and emit a second band 325 of electromagnetic radiation. The second end of the optic 315 is adapted for contacting biological tissue 385 and delivering the second band 325 of electromagnetic radiation to treat the biological tissue 385. The optic 303, first end 305, fluorescent material 310, second end 315, first band 320 of electromagnetic radiation, and second band 325 of electromagnetic radiation can include any one or more of the features of respective elements optic 100, 203, first end 105, 205, fluorescent material 110, 210, second end 115, 215, first band 120, 220 of electromagnetic radiation, second band 125, 225 of electromagnetic radiation and filter 230 discussed in connection with FIGS. 1 and 2.

Various elements shown in the exemplary apparatus 300 of FIG. 3 include a light source 345, a reflector 350, a second reflector 355, a second fluorescent material 360, and a cooling element 365.

The light source 345 is disposed relative to the filter 330 and is adapted to provide the first band 320 of electromagnetic radiation. In embodiments without a filter, such as the embodiment shown in FIG. 1, a light source is disposed relative to the first end. In various embodiments, the light source 345 can be any one or more of a UV light source, visible light source, flash lamp, continuous lamp, Xe lamp, Kr lamp, laser (e.g., Nd:YAG laser, diode, diode array, Ar ion laser), and a non-laser diode. In other words, the light source 345 can be monochromatic or polychromatic, can be coherent or incoherent, and can be continuous or pulsed.

In various embodiments, the light source 345 provides a single wavelength or band of wavelengths (e.g., a first band 320 of electromagnetic radiation) that are substantially absorbed by the fluorescent material 310. In such embodiments, the wavelength or wavelengths provided by the light source 345 are the first band 320 of electromagnetic radiation, and a filter 330 is not necessary.

In some embodiments, the light source 345 provides a wavelength or band of wavelengths that are absorbed by the fluorescent material 310 (e.g., a first band 320 of electromagnetic radiation), as well as other wavelengths. In such embodiments, the wavelength or wavelengths provided by the light source 345 include the first band 320 of electromagnetic radiation, but filter 330 is necessary for preventing the other (e.g., harmful or otherwise undesirable) wavelengths from reaching the biological tissue. In one embodiment, the filter 330 reflects the other wavelengths back into the light source 345 (e.g., a flash lamp), to heat the light source and improve the emissions of the light source.

The reflector 350 is disposed relative to a surface (e.g., at least one lateral surface) of the optic between the first end 305 and the second end 315. The reflector 350 is adapted to reflect electromagnetic radiation 370 (e.g., at least a portion of the first band 320 or at least a portion of the second band 325 of electromagnetic radiation), which is traveling on a path away from the second end 315 back into the optic 303 and, in some cases, back into the fluorescent material 310. In some embodiments, the reflector 350 reflects electromagnetic radiation to the biological tissue. Accordingly, the reflector 350 can increase the output efficiency of the optic 303 by increasing the conversion efficiency of the first band 320 into the second band 325 of electromagnetic radiation, and by increasing the delivery efficiency of the second band 325 of electromagnetic radiation to the biological tissue. In one embodiment, a reflector can be disposed on any surface of an optic except the second end.

The reflector 350 can include one or more layers of a metal or oxide. A reflector can include at least one of a metal (e.g., aluminum, gold, silver), a ceramic, and a white material. A reflector 350 can be at least partially absorbing and/or at least partially transparent. Note, however, in various embodiments an optic 100, 203, 303 can exhibit total internal reflection, which can reduce or eliminate the need for a reflector 350.

The second reflector 355 is disposed relative to the light source 345, to reflect a portion 375 of electromagnetic radiation provided by the light source 345. In some embodiments, the second reflector 355 can reflect the portion 375 of electromagnetic radiation towards the first end 305. In certain embodiments, the second reflector 355 can reflect the portion 375 of electromagnetic radiation back into the he light source 345, to heat the light source 345 and improve the emissions of the light source 345. Similarly, in some embodiments, the filter 330 can reflect the portion 375 of electromagnetic radiation back into the he light source 345, to heat the light source 345 and improve the emissions of the light source 345.

The second fluorescent material 360 is disposed relative to the filter 330, between the filter 330 and the light source 345. In various embodiments, the second fluorescent material 360 can have any one or more features or properties of optics 100, 203, 303. The second fluorescent material 360 can include a uranium doped glass or crystal. The second fluorescent material 360 can include an element capable of converting UV light into visible light, for example, a fluorescent glass such as LUMILASS-R7/G9/B manufactured by Sumita Optical Glass, Inc. The second fluorescent material 360 can include a fluorescent dye (e.g., in a liquid, gel, or polymer) such as the dyes described in connection with the fluorescent material 110. The second fluorescent material 360 can also include any of the polymers, glasses, or crystals discussed in connection with the fluorescent material 110.

In various embodiments, the second fluorescent material 360 can increase the operating efficiency of the apparatus 300 by increasing the fraction of electromagnetic radiation emitted from the light source 345 that is delivered to the biological tissue as the second band 325 of electromagnetic radiation. The second fluorescent material 360 can prevent harmful, non-therapeutic, or otherwise undesirable wavelengths from reaching the biological tissue. For example, the light source 345 can have an emission band 380 that includes a wavelength outside of the first band 320, and the second fluorescent material 360 can convert the wavelength into a wavelength inside of the first band 320.

In an embodiment without a filter (e.g., optic 100 shown in FIG. 1), a second fluorescent material can be disposed between an optic and a light source.

A cooling element 365 can modulate the temperature in a region of skin and/or minimize unwanted thermal injury to untargeted skin. For example, the cooling element 365 can cool the skin before, during, or after delivery of electromagnetic radiation, or a combination of the aforementioned. Cooling can be to a predetermined temperature and depth within the biological tissue, to control the pattern of thermal injury induced within the tissue. A cooling element 365 can modulate the temperature in a region of an apparatus 300, to improve the function of the apparatus 300. For example, the cooling element 365 can cool the optic 303 or the fluorescent material 310, to improve the conversion efficiency of the fluorescent material 310 (e.g., dissipate heat caused by absorption of the first beam, where the heat decreases the conversion efficiency or shift an emission wavelength of the fluorescent material 310).

The cooling element 365 can be adapted to cool the biological tissue (not shown), the optic 303, or both the biological tissue and the optic 303. The cooling element 365 is shown diagrammatically as in thermal contact with the optic 303 through the reflector 350. However, virtually any arrangements where the cooling element 365 or a coolant (e.g., a spray from the cooling element 365) is in thermal contact with at least one of the biological tissue or the optic 303 is possible. In one example, the cooling element 365 can directly contact the biological tissue or the optic 303. The cooling element 365 can be a Peltier element or a piece of ice or at least a portion of the optic 303 (e.g., a pre-cooled sapphire). In one embodiment, a cooling element can directly or indirectly cool a filter, a reflector, or any one or more elements of an apparatus.

In another example, the cooling element 365 can function by applying, circulating, or spraying a liquid or gas to the biological tissue or the optic 303. The cooling element 365 can include a radiator or a passage for flowing coolant or a spray cryogen. The cooling element 365 can include an air flow. The cooling element 365 can include a fluorocarbon type cooling fluid, which can be transparent to the electromagnetic radiation used. A spray cooling device can use cryogen, water, or air as a coolant. In one embodiment, a dynamic cooling device (e.g., a DCD™ available from CANDELA® Corporation) can cool the skin. For example, the apparatus 300 can include tubing for delivering a cooling fluid to the optic 303 or the biological tissue. The tubing can be connected to a container of a low boiling point fluid, and the apparatus can include a valve for delivering a spurt of the fluid to the skin. Heat can be extracted from the skin by evaporative cooling of the low boiling point fluid. In one embodiment, the fluid is a non-toxic substance with high vapor pressure at normal body temperature, such as a Freon or tetrafluoroethane.

Note that electromagnetic radiation can travel substantially along a single axis. First, electromagnetic radiation travels from the light source 345 to the fluorescent material 310 where the first band is converted into the second band and other wavelengths are blocked. Then, the second band travels (e.g., along the same axis or in the same direction) to the biological tissue 385. Electromagnetic radiation from the light source 345 need not reach the biological tissue. Such an arrangement is possible because wavelengths of electromagnetic radiation that are harmful, non-therapeutic, or otherwise undesirable do not substantially reach and/or do not substantially pass through the optic and reach the biological tissue (i.e., they are substantially not included in the second band 325 of electromagnetic radiation).

Figure 4:
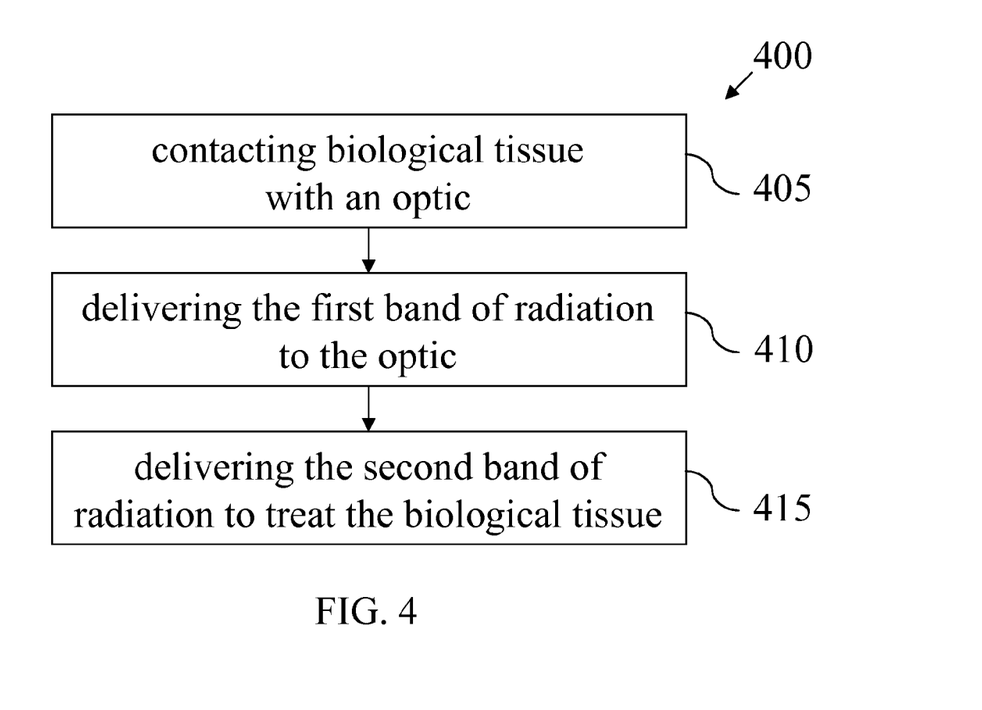
FIG. 4 shows an exemplary method for treating biological tissue.

FIG. 4 shows an exemplary method 400 for treating biological tissue. The method 400 includes: step 405 of contacting biological tissue with an optic having a fluorescent material adapted to substantially absorb a first band of electromagnetic radiation and to emit a second band of electromagnetic radiation; step 410 of delivering the first band of electromagnetic radiation to the optic, to cause the optic to emit the second band of electromagnetic radiation; and step 415 of delivering the second band of electromagnetic radiation to treat the biological tissue. In general, the method 400 can employ any of the apparatuses discussed in connection with FIGS. 1-3.

In various embodiments, the method 400 includes selecting a fluorescent body to emit the second band of electromagnetic radiation matched to a chromophore within the biological tissue. For example, a second band of electromagnetic radiation can be absorbed by one or more of hemoglobin, melanin, porphyrin, collagen, exogenous pigment, and water. The second band of electromagnetic radiation can be absorbed preferentially over adjacent tissue biological tissue.

In some embodiments, the method includes (i) delivering the first band of electromagnetic radiation through a filter disposed relative to a first end of the optic, the filter adapted to substantially transmit the first band of electromagnetic radiation to the fluorescent material and to block other electromagnetic radiation and (ii) delivering the second band of electromagnetic radiation to the biological tissue through a second end of the optic, the second end contacting the biological tissue. For example, the filter can be an element like filter 230, 330 described in connection with FIGS. 2 and 3.

In certain embodiments, the method includes delivering a therapeutically effective amount of the second band of electromagnetic radiation to treat the biological tissue. A therapeutically effective amount can be an amount necessary to eliminate, inhibit, or reverse the indication being treated. A therapeutically effective amount can be delivered in a single session, or in multiple sessions, of treatment. Alternatively, a therapeutically effective amount can be defined by a predetermined endpoint for treatment such as a predetermined temperature or a predetermined visual indicator (e.g., a change in coloration or other property of the biological tissue).

In various embodiment, methods can include cooling the biological tissue, the optic, or both the biological tissue and the optic. For example, the biological tissue an optic can be cooled by a cooling system like cooling element 365 described in connection with FIG. 3.

In some embodiments, such as method 400, pressure can be applied to substantially remove air intervening the biological tissue and the optic. Removing air intervening the biological tissue and the optic can facilitate treatment because removing air can reduce scattering of the second beam of electromagnetic radiation and thus increase the proportion of the second beam of electromagnetic radiation that reaches the biological tissue. Accordingly, it is not necessary to remove all of the air intervening the biological tissue and the optic (e.g., a de minimus amount of intervening air is compatible with the invention).

Figure 5:
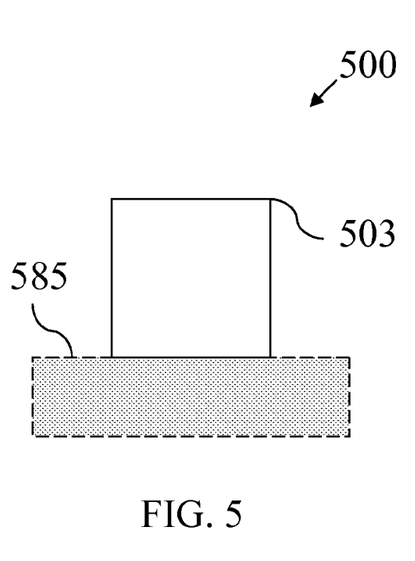
FIG. 5 shows an optic contacting biological tissue.

FIG. 5 diagrams an embodiment 500 where pressure is applied to an optic 503 contacting biological tissue 585, to substantially remove air intervening the biological tissue 585 and the optic 503. In one embodiment, pressure can be manual (e.g., applied by the user) or mechanical (e.g., applied by a spring or piston). In another embodiment, pressure can be pneumatic device (e.g., applied by a pneumatic device such as a Pneumatic Skin Flattening Technology (PSF™) device available from CANDELA® Corporation). A pneumatic (e.g., PSF™) device can have an additional advantage of blocking pain signals to the brain by creating a vacuum through a chamber that pushes blood away from the treatment.

In certain embodiments, the method 400 includes applying an index matching element between the optic and the biological tissue, to facilitate delivering the second band of electromagnetic radiation to the biological tissue. An index matching element can function to remove air intervening the biological tissue and the optic and to mitigate scattering of the second beam of electromagnetic radiation traveling from the optic to the biological tissue.

Figure 6:
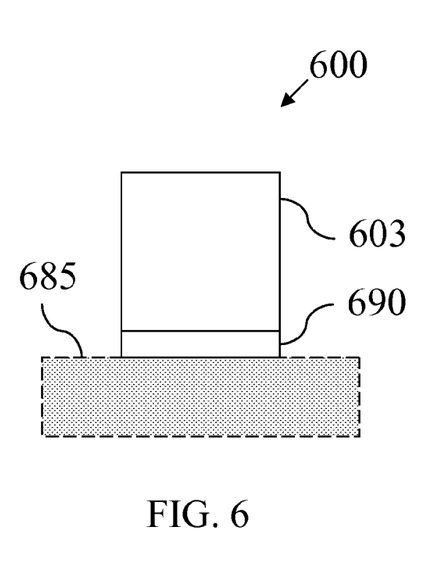
FIG. 6 shows an index matching element between an optic and biological tissue.

FIG. 6 diagrams an embodiment 600 where an index matching element 690 is applied between an optic 603 and biological tissue 685. An index matching element can be water, an aqueous or organic (e.g., alcohol) based solution (e.g., of an analgesic or salve), a gel, or an oil. An index matching element can also include additives and/or surfactants. An index matching element 690 can be adapted to transfer heat from the skin. For example, the index matching material 690 can incorporate a photodynamic therapy compound such as for example alpha leulenic acid (ALA) available from DUSA. ALA can also be applied into or at least on to the skin prior to treatment and also prior to applying index matching material 690. In various embodiments, any of the optics and apparatuses shown in FIGS. 1-3 can include an index matching element 690.

In various embodiments, the invention also includes a method for physio-chemically modifying an object with electromagnetic radiation. The method includes contacting the object with an optic having a fluorescent material adapted to substantially absorb a first band of electromagnetic radiation and to emit a second band of electromagnetic radiation. The method also includes delivering the first band of electromagnetic radiation to the optic, to cause the optic to emit the second band of electromagnetic radiation. Furthermore, the method includes delivering a predetermined amount of the second band of electromagnetic radiation to the object.

In some embodiments, the invention also includes a method for providing electromagnetic radiation capable of treating biological tissue. The method includes contacting the biological tissue with a device including an optic, the optic having a fluorescent material adapted to substantially absorb a first band of electromagnetic radiation and to emit a second band of electromagnetic radiation. The method also includes delivering the first band of electromagnetic radiation to the optic, to cause the optic to emit the second band of electromagnetic radiation.

For example, various treatments are possible with a Ti-sapphire crystal as the fluorescent material. First, permanent hair removal can be achieved using a Ti-sapphire crystal, a 30-50 $J/cm^2$ fluence, and a 40 ms pulse width. Second, long term (e.g., non-permanent) hair removal can be achieved using a Ti-sapphire crystal, a 20 $J/cm^2$ fluence, and a 25 ms pulse width. Third acne can be treated using a Ti-sapphire crystal, a 30 $J/cm^2$ fluence, and a 60 ms pulse width. Fourth, inflammation can be treated using a Ti-sapphire crystal, a 15-20 $J/cm^2$ fluence, and a 100 ms pulse width. These examples are intended to be illustrative, not limiting, and virtually any skin treatment is possible given a fluorescent material selected to emit an appropriate wavelength and the fluence and pulse width are appropriate for the desired treatment.

In certain embodiments, the invention includes a kit for treating biological tissue. The kit includes an apparatus including (i) an optic having a first end, a second end, and a fluorescent material, the fluorescent material adapted to substantially absorb a first band of electromagnetic radiation and emit a second band of electromagnetic radiation and (ii) a filter disposed relative to the first end of the optic and adapted to substantially transmit the first band of electromagnetic radiation to the fluorescent material and to block other of electromagnetic radiation. The kit also includes instruction means for contacting the biological tissue with a second end of the optic and delivering the second band of electromagnetic radiation to treat the biological tissue. In one embodiment, the kit can include an apparatus such as the apparatus such as the apparatus described in connection with FIG. 3.

In general, instruction means can include instructions for delivering electromagnetic radiation to biological tissue, to treat the biological tissue. Instructions can include instructions for operating systems, devices, treatments according to the invention. Instructions can also prescribe parameters such as wavelength, power density, pulse duration, and/or cooling parameters for treatment of the target region. For example, instruction can prescribe parameters for treating a particular indication or a particular skin type.

The instruction means (e.g., treatment and/or operation guidelines) can be provided in any form that conveys the requisite information. Instruction means can be audio, for example spoken word, recorded in analog or digital form (e.g., audio recording), or received and/or transmitted in analog or digital form (e.g., by telephone, conference call, or audio signal transmitted over a network). Instruction means can also be visual or video, for example hard-copy (e.g., as a leaflet, booklet, book, manual, recorded medium, and the like) or soft-copy (e.g., recorded in analog or digital form as a file recorded on an optical, electronic, or computer readable medium such as a disk drive, CD-ROM, DVD, and the like). Additionally, instruction means can be interactive or real-time (e.g., a teleconference or internet chat).

The instruction means can be implemented in digital electronic circuitry, or in computer hardware, firmware, software, or in combinations thereof. The implementation can be as a computer program product, e.g., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and the computer program can be deployed in any form, including as a stand-alone program or as a subroutine, element, or other unit suitable for use in a computing environment. A computer program can be deployed to be executed on one computer or on multiple computers at one site.

The instruction means can be performed by one or more programmable processors executing a computer program to perform functions of the invention by operating on input data and generating output. The instruction means can also be performed by, and an apparatus can be implemented as, special purpose logic circuitry, e.g., an FPGA (field programmable gate array) or an ASIC (application-specific integrated circuit). Subroutines can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer also includes, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element).

Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The methods can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the internet, and include both wired and wireless networks.

The computing system can include clients and servers. A client and a server are generally remote from each other and typically interact through a communication network. The relationship of client and server arises by virtue of computer programs running on the respective computers and having a client-server relationship to each other.

While the invention has been particularly shown and described with reference to specific embodiments, it should be understood by those skilled in the art that various changes in form and detail may be made without departing from the spirit and scope of the invention as defined by the appended claims.

What is claimed is:

1. An optic comprising a first end, a fluorescent material, and a second end, the first end adapted to transmit a first band of electromagnetic radiation to the fluorescent material, the fluorescent material comprising an input end and an output end and adapted to absorb the first band of electromagnetic radiation and emit a second band of electromagnetic radiation, and the output end of the fluorescent material adapted to contact biological tissue and deliver the second band of electromagnetic radiation to treat the biological tissue.

2. The optic of claim 1, further comprising a reflector disposed relative to at least one surface of the optic, the reflector for reflecting at least a portion of the second band of radiation, to direct the portion towards the biological tissue.

3. An apparatus for treating biological tissue, the apparatus comprising:
   an optic comprising a first end, a second end, and a fluorescent material, the fluorescent material comprising an input end and an output end and adapted to substantially absorb a first band of electromagnetic radiation and emit a second band of electromagnetic radiation;
   a filter disposed relative to the first end of the optic and adapted to substantially transmit the first band of electromagnetic radiation to the fluorescent material and to block other electromagnetic radiation; and
   wherein the output end of the fluorescent material is configured to contact the biological tissue and deliver the second band of electromagnetic radiation to treat the biological tissue.

4. The apparatus of claim 3, wherein the filter is a coating on a surface of the first end.

5. The apparatus of claim 3, wherein the filter is a dichroic element.

6. The apparatus of claim 3, wherein the filter can block a portion of the second band of electromagnetic radiation, to direct the portion towards the biological tissue.

7. The apparatus of claim 3, further comprising a reflector disposed relative to a surface of the optic between the first end and the second end, the reflector adapted to reflect the second band of electromagnetic radiation.

8. The apparatus of claim 3, further comprising a light source disposed relative to the filter, the light source adapted to provide the first band of electromagnetic radiation.

9. The apparatus of claim 8, further comprising a reflector disposed relative to the light source, to direct a portion of the first band of electromagnetic radiation to the fluorescent material.

10. The apparatus of claim 3, further comprising a cooling element adapted to cool the biological tissue, the optic, or both the biological tissue and the optic.

11. The apparatus of claim 3, further comprising an index matching element disposed relative to the second end, the index matching element adapted to facilitate delivering the second band of electromagnetic radiation to the biological tissue.

12. The apparatus of claim 3, further comprising a second fluorescent material disposed relative to the filter.

13. The apparatus of claim 3, wherein the second band of electromagnetic radiation is characterized by a pulse width greater than about 1 ms.

14. The apparatus of claim 3, wherein the second band of electromagnetic radiation is characterized by a pulse width between about 1 ms and about 120 ms.

15. The apparatus of claim 3, wherein the second band of electromagnetic radiation is characterized by a fluence between about 1 J/cm$^2$ and about 100 J/cm$^2$.

* * * * *